United States Patent [19]

Andres et al.

[11] Patent Number: 5,186,868
[45] Date of Patent: Feb. 16, 1993

[54] METHODS FOR TRITIUM LABELING

[75] Inventors: Hendrik Andres, Hochwald, Switzerland; Hiromi Morimoto, El Cerrito; Philip G. Williams, Oakland, both of Calif.

[73] Assignee: The Regents of the University of California, Oakland, Calif.

[21] Appl. No.: 505,257

[22] Filed: Apr. 5, 1990

[51] Int. Cl.$^5$ ............................................. G21G 4/08
[52] U.S. Cl. .................................. 252/645; 424/1.1; 423/646; 423/647.7
[58] Field of Search ..................... 252/645; 424/1.1; 423/646, 647.7

[56] References Cited

U.S. PATENT DOCUMENTS

| | | | |
|---|---|---|---|
| 2,504,927 | 4/1950 | Hansley | 423/646 |
| 2,606,100 | 8/1952 | Alexander | 423/646 |
| 2,702,281 | 2/1955 | Gibb | 423/646 |
| 3,009,971 | 11/1961 | Mottlau | 585/700 |
| 3,132,188 | 5/1964 | Cook | 585/469 |
| 3,210,288 | 10/1965 | Evans et al. | 252/301.1 |
| 3,214,486 | 10/1965 | Doyle et al. | 585/500 |
| 3,387,933 | 6/1968 | Snyder | 423/646 |
| 3,728,272 | 4/1973 | Casensky | 423/646 |
| 3,919,405 | 11/1975 | Lenz et al. | 423/646 |
| 3,966,781 | 6/1976 | Atkinson et al. | 260/410.9 R |
| 3,995,017 | 11/1976 | Hoetslander et al. | 423/648 |
| 3,998,941 | 12/1976 | Nelson | 423/646 |
| 4,007,257 | 2/1977 | Lemieux et al. | 423/646 |
| 4,020,003 | 4/1977 | Steinberg et al. | 252/301.1 |
| 4,162,142 | 7/1979 | Ehrenkaufer et al. | 260/326.2 |
| 4,889,660 | 12/1989 | Jensen et al. | 252/646 |

OTHER PUBLICATIONS

Novakova et al., Isotopic Exchange of Gas Deuterium with latice Hydrogen of Hydrides, Mar. 1970, pp. 520–527.
Holding et al., The Laboratory Preparation of Lithium Deuterium and Lithium Aluminum Deuterium, May 1958, pp. 321–324.
Brown, H. C. et al., (1980) *J. Org. Chem.* 45:1–12.
Brown, H. C. et al., (1979) *Aldrichimica Acta* 12:3–11.
Brown, H. C. et al., (1973) *J. Am. Chem. Soc.* 95:1669–1671.
Fortunato, J. M. et al., (1975) *J. Org. Chem.* 41:2194–2200.
Hegde, S. et al., (1983) *J. Chem. Soc. Chem. Commun.* 1484–1485.
Coates, R. M. et al., (1986) *Syn. and Ap. Isotopically Labeled Compounds* (Proc. 2nd Int. Symp.) 207–212.
Coates, R. M. et al. (1982) *Syn. and Ap. Isoptically Labeled Compounds* (Proc. Int. Symp.) 429–430.
Ferrell, E. et al. (1934) *J. Chem. Soc.* 7–8.
Cao, G. Y. et al., (1984) *Trans. Am. Nucl. Soc.* 45:18–19.
Moser, H. C. et al., (1962) *J. Chem. Phys.* 66:2272–2273.
Bowman, R. C. et al., (1988) *J. Nucl. Materials* 154:318–331.
Brown, H. C. et al., (1978) *J. Am. Chem. Soc.* 100:3343–3349.
Brown, H. C. et al., (1970) *J. Am. Chem. Soc.* 92:709–710.
Altman, L. J. et al., (1980) *Anal. Chem.* 52:992–995.
Klusener, P. et al., (1986) *Angew. Chem.* (English Edition) 25:465.
Pi, R. et al., (1987) *J. Org. Chem.* 52:4299–4303.
Williams, P. G. et al., (1989) *Trans. Am. Nucl. Soc.* 60:34–36.
Williams, P. G. et al., (1988) *J. Am. Chem. Soc.* 110:8038–8044.
Bloxsridge, J. P. et al., (1981) *Org. Magn. Reson.* 15:214–217.
Bloxsridge, J. P. et al., (1981) *Org. Magn. Reson.* 12:574–578.
Andres, H. et al., (1990) "Preparation and Use of LiEt$_3$BT and LiAlT$_4$ at Maximum Specific Activity" in *J. Chem. Soc. Commun.* 627–628.

*Primary Examiner*—Brooks H. Hunt
*Assistant Examiner*—Ngoclan T. Mai
*Attorney, Agent, or Firm*—Morrison & Foerster

[57] ABSTRACT

Reagents and processes for reductively introducing deuterium or tritium into organic molecules are described. The reagents are deuterium or tritium analogs of trialkyl boranes, borane or alkali metal aluminum hydrides. The process involves forming these reagents in situ from alkali metal tritides or deuterides.

9 Claims, 3 Drawing Sheets

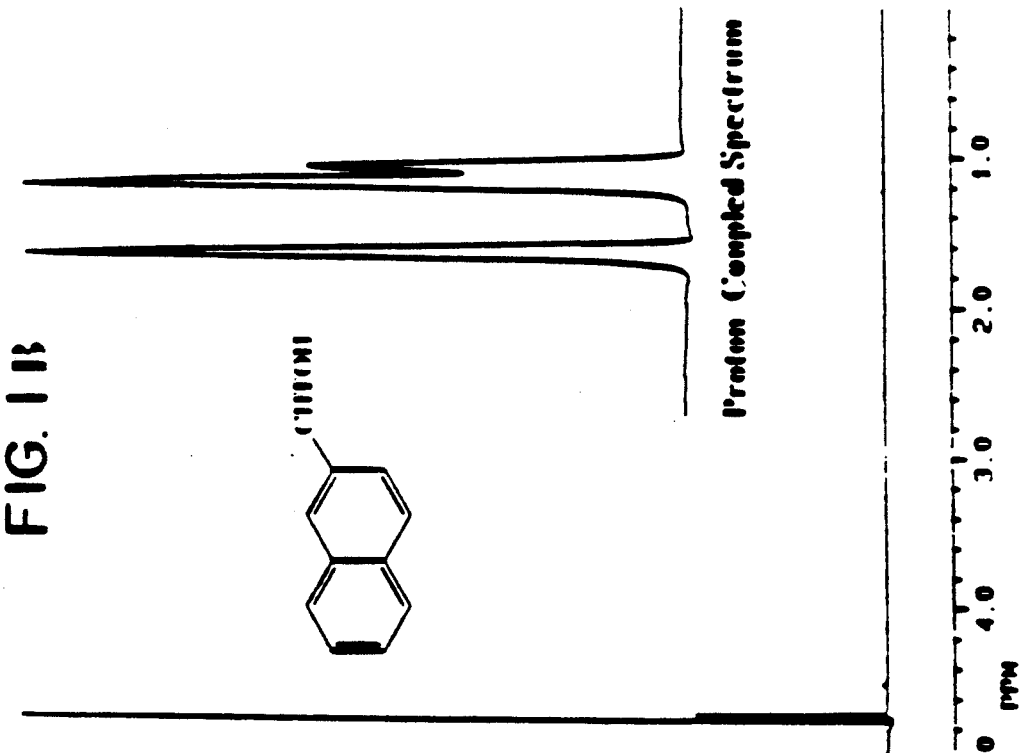
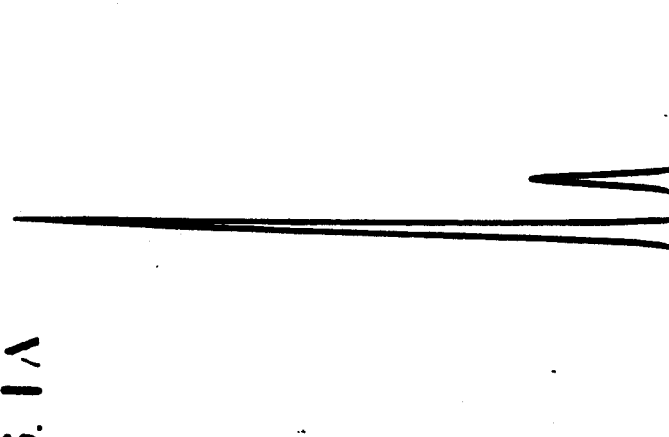
FIG. 1A  FIG. 1B  FIG. 1

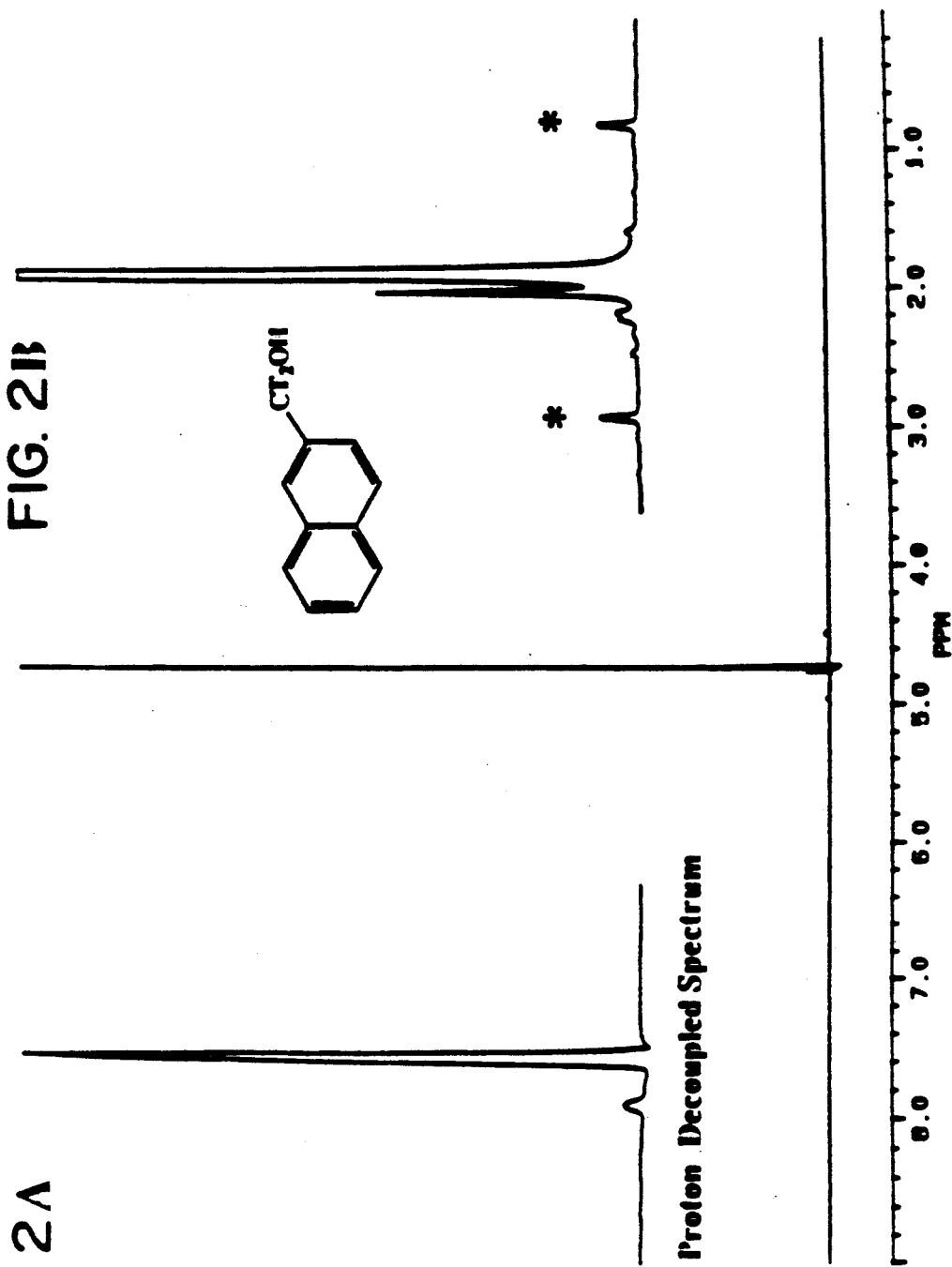

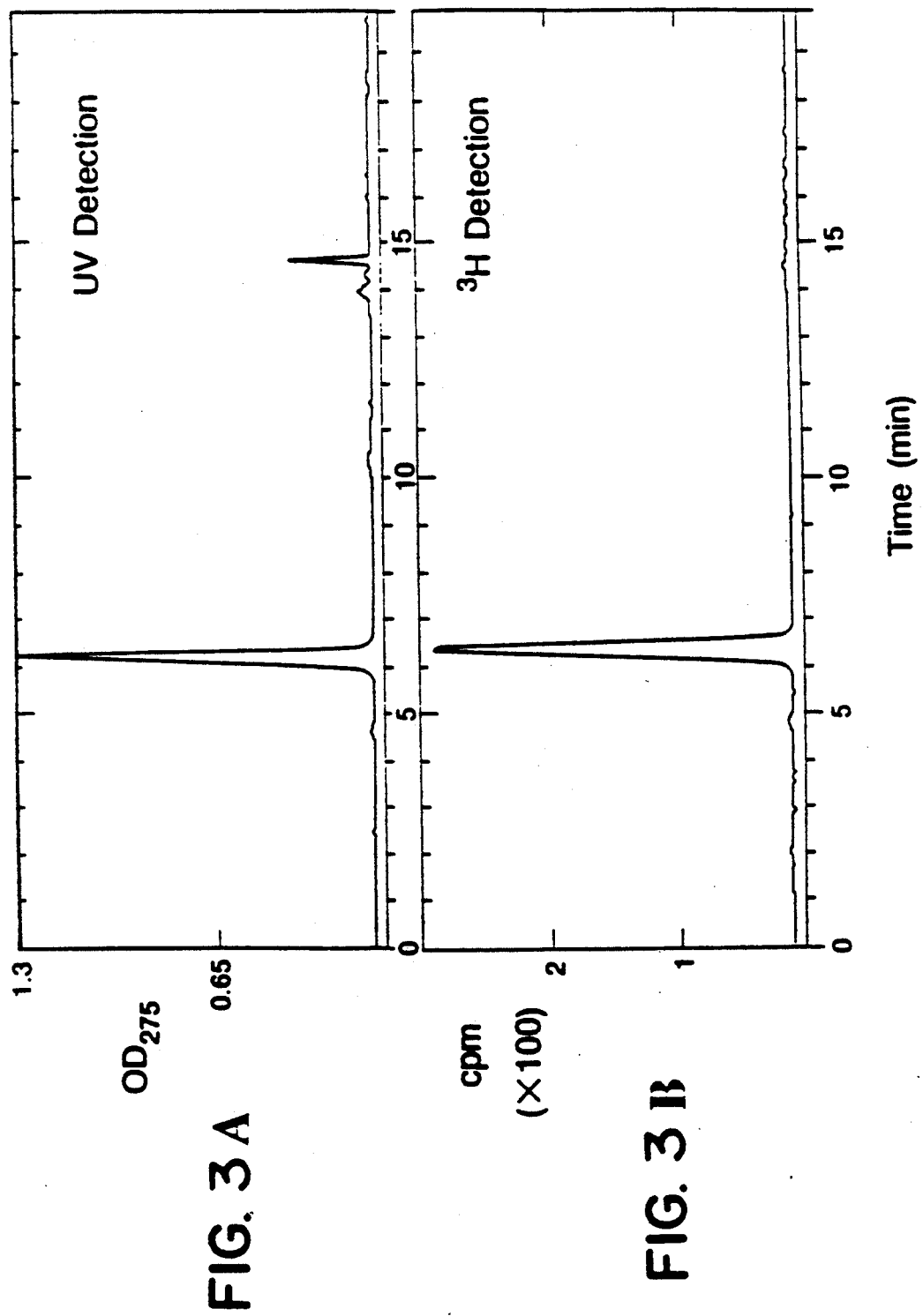

METHODS FOR TRITIUM LABELING

REFERENCE TO GOVERNMENT INTEREST

This research was partly supported by a grant from the U.S. National Institutes of Health. It was performed at Lawrence Berkeley Laboratory under contract DE-AC03-76SF00098. The United States government may have rights to this invention.

TECHNICAL FIELD

This invention involves agents useful for preparing isotopically labeled compounds. More particularly, it relates to novel site-selective deuterating and tritiating agents with high deuterium or tritium contents, methods for their preparation, and methods for using these agents to insert high levels of deuterium/tritium labels into reducible compounds.

BACKGROUND ART

Isotopic labeling is a useful tool for rendering organic compounds easily identifiable in analytical and biochemical schemes. The isotopic label may be detected very sensitively, especially in the case of a radionuclide. By placing the isotopic label in a specific site in a molecule, it is possible to study reactions involving the molecule and detect and delineate reaction paths. Traditionally, isotopic hydrogen (e.g., tritium or deuterium) labeling has been limited by the unavailability of adequate deuterating/tritiating agents.

There are two fundamental techniques for introducing isotopic hydrogen into organic molecules. These are synthetic techniques and exchange techniques. Synthetic techniques, where tritium or deuterium is directly and specifically inserted, yield high tritium or deuterium abundance, but are limited by the chemistry required. In addition, the molecule being labeled may be changed, depending upon the severity of the synthetic reaction employed. Exchange techniques yield lower tritium or deuterium incorporation, often with the isotope being distributed over many sites on the molecule, but offer the advantage that they do not require separate synthetic steps and are less likely to disrupt the structure of the molecule being labeled.

Three common synthetic methods for incorporating activity levels of tritium into target molecules have been: (1) "hydrogenation" of the target molecule using tritium gas ($T_2$), with a catalyst; (2) tritiodehalogenation; and (3) tritiomethylation with $CT_3I$. Each of these methods has been heavily employed in the art to achieve high levels of isotope incorporation, yet each involves reaction conditions that can affect the integrity of the target molecule. Conversely, the use of milder "tritium exchange" methods typically involves reduction in the level of tritium incorporated into the target molecule.

A fourth way of synthetically incorporating tritium into a target molecule which contains a reducible site is to contact the target molecule with a reducing agent which is capable of inserting one or more tritium atoms into the reducible site. This methodology essentially mimics reduction with hydrogen-inserting reducing agents.

Metal borohydrides such as $LiAlH_4$ and $NaBH_4$ are widely used mild reducing agents. In contrast, lithium trialkylborohydride (superhydride) (Brown, H. C. et al., (1980) *J. Org. Chem.* 45:1-12) is known to be a highly reactive nucleophilic reducing agent, and is now commonly used in organic synthesis (Brown, H.C. et al., (1979) *Aldrichimica Acta* 12:3-11). This reagent is capable of reducing esters, hindered alkyl halides (Brown, H.C. et al., (1973) *J. Am. Chem. Soc.* 95: 1669-1671) and toluene-p-sulphonates, in addition to exhibiting great sterioselectivity and steriospecificity, as in the reduction of epoxides. More hindered trialkylborohydrides (such as lithium or potassium tri-sec-butyl borohydride; known as L-selectride and K-selectride) exhibit even more steric control, as in the reduction of cyclic ketones (Fortunator, J. M. et al., (1975) *J. Org. Chem.* 41: 2194-2200). These remarkable hydride reducing agents are generally synthesized by reaction of the appropriate alkylborane with a metal hydride (Brown, H. C. et al (1980) *J. Org. Chem.* 45:1-12). It is clear that the ability to produce metal deuterides and tritides with high deuterium/tritium content would give access to a large number of deuteriated/tritiated reducing agents for chemoselective, regioselective and stereoselective labeling sequences, and allow high level deuterium/tritium incorporation through established synthetic routes with these highly reactive and selective reagents.

The utility of supertritide has been demonstrated (Hegde, S. et al., (1983) *J. Chem. Soc. Chem. Commun.*, 1484-1485) by the reduction of acids, aldehydes, toluene-p-sulphonates and epoxides, but these reactions were conducted with supertritide of specific activities in the mCi/mmol range (100's of MBq/mmol). Later work (Coates, R. M. et al., (1986) *Synthesis and Applications of Isotopically Labeled Compounds (Proc. 2nd Int. Symp.)*, 207-212) reported the synthesis of chiral methyl groups, starting with supertritide at approximately 3 Ci/mmol. This is still a factor of 10 below the theoretical maximum (one tritium atom per molecule gives a specific activity 28.72 Ci/mmol or 1063 GBq/mmol) and consequently this tritiation reagent has not been applied in those types of reactions where it is used in general chemistry. The same general statements are true for the availability and utility of $LiAlT_4$. At this time, both $LiAlD_4$ and $LiEt_3BD$ are available commercially.

Although the complex hydrides are very useful reagents, the preparation of the initial metal hydrides has been problematic, especially where radioisotopes are involved. Metal hydrides may be prepared from the respective elements: e.g. atomic hydrogen produced in a glow discharge tube was found to rapidly react with various alkali metals, vacuum condensed as thin films on the reaction tube walls, to form metal hydrides (Ferrell, E. et al., (1934) *J. Chem. Soc.* 7-8). Other means of producing atomic hydrogen (or tritons) include dissociation of molecular hydrogen (tritium) by microwave discharge activation (Cao, G. Y. et al., (1984) *Trans. Am. Nucl. Soc.* 45:18-19) or on the surface of a hot tungsten wire (Moser, H. C. et al., (1962) *J. Chem. Phys.* 66:2272-2273). The latter two methods offer the advantages of being less limiting in scale and the option of exchange of tritons with LiH, thereby avoiding the use of liquid lithium. Tritide synthesis on a large scale has also been reported under conditions of high temperature and pressure, where lithium tritide was synthesized at 98% purity in an iron crucible at 750° C., in the presence of three atmospheres of tritium gas (Bowman, R. C. et al., (1988) *J. Nucl. Materials* 154:318-331). The severe conditions and need for excessive tritium in this procedure make this option less attractive than the others outlined above, and only usable by the nuclear/fusion industries.

One other problem lies in the fact that once the hydride (deuteride or tritide) is formed by one of the above methods its chemical reactivity is reported to be low, and conversion into a complex hydride for use as a reducing reagent in organic synthesis may be sluggish. Hegde, S. et al., (1983) *J. Chem. Soc. Chem. Commun.*, 1484-1485, reported that a typical reduction with such agents took several days at 150° C.

The present invention is directed to the aforementioned problems. It provides a new method of in situ synthesis to generate a highly reactive alkali metal deuteride or tritide with a large proportion of its hydrogen present as deuterium or tritium from the respective deuterium or tritium gas. This material is then converted into a desirable highly selective labeling agent.

DESCRIPTION OF THE PRIOR ART

Background References. Brown, H. C. and Krishnamurthy, S., (1979) *Aldrichimica Acta* 12:3-11 presents a good summary of the state of borane chemistry for organic reductions, including the increased ability to perform regioselective, stereoselective and chemoselective reductions of various organic functional groups.

Selective Borohydride Reducing Agents. The synthesis of Superhydride is described in Brown, H. C. et al., (1980) *J. Org. Chem.* 45:1-12, and some of its uses are described in Brown, H. C. and Krishnamurthy, S., *J.* (1973) *Am Chem. Soc.* 95:1669-1671. L-Selectride and K-Selectride are described synthetically in Brown, H. C. et al., (1978) *J. Am. Chem. Soc.* 100:3343, and some of their uses are described in Fortunato, J. M. and Ganem, B. (1976) *J. Org. Chem.* 41: 2194-2200, and Brown, H. C. and Dickason, W. C., (1970) *J. Am. Chem. Soc.* 92:709.

Tritium Labeling Agents. The synthesis of a low specific activity "Supertritide" (LiEt$_3$BT) is described in Hegde, S. et al., (1983) *J. Chem. Soc., Chem. Comm.* 1983:1484-1485, and see Coates, R. M. et al., in "Synthesis and Applications of Isotopically Labeled Compounds (Proc 2d Int'l Symp.)". pp. 207-212 Muccino, R. R., ed. (Elsevier Press: Amsterdam) (1986). Altman, L. J. and Thomas, L., (1980) *Anal. Chem.* 52:992-995 identified a high specific activity sodium borotritide (NaBT$_4$).

Reactive Lithium Hydride. Klusener, P. et al., (1986) *Angew. Chem. (English Edition)* 25:465, and Pi, R. et al., (1987) *J. Org. Chem.* 52:4299-4303 have reported a method of in situ synthesis of lithium hydride by bubbling hydrogen gas through a solution of n-butyllithium in hexane in the presence of tetramethylethylenediamine (TMEDA). The resulting hydride is a fine suspension and is highly reactive at room temperature.

RELATED PUBLICATIONS

In November of 1989, the present inventors and a colleague published a report of some of the work described herein in *Trans. Am. Nucl. Soc.* 60:34-36 (1989).

SUMMARY OF THE INVENTION

It is accordingly a primary object of the present invention to overcome the disadvantages of the prior art and to provide methods and reagents which are capable of tritium and deuterium labeling selected specific sites in target molecules, while achieving the labeling at high levels of tritium and deuterium insertion.

Additional objects, advantages and novel features of the invention will be set forth in part in the description which follows, and in part will become apparent to those skilled in the art upon examination of the following, or may be learned by practice of the invention.

The process of the invention is characterized as involving the in situ generation of highly selective reducing agents from alkali metal tritides or deuterides which have in turn formed from alkali metal alkyls.

Thus, in one aspect, the invention provides a process for introducing tritium or deuterium label into organic compounds having a reducible site. This process involves reacting an organic solvented solution of an alkali metal alkyl with a gas which contains tritium or deuterium in the presence of an alkyl tertiary amine. This gives rise to an alkali metal tritide or deuteride. This tritide or deuteride can then be reacted in any of several manners to give rise to a reactive labeling reducing agent. In one of these subsequent reactions the alkali metal tritide or deuteride is reacted with a solution of trialkylborane thereby forming an alkali metal trialkyl borotritide or borodeuteride which can serve as the reducing agent. In another of the subsequent reactions the alkali metal tritide or deuteride is reacted with a solution of aluminum halide thereby forming a solution of alkali metal aluminum tritide or deuteride reducing agent. In a third such reaction the alkali metal tritide or deuteride is reacted with boron trifluoride thereby forming the tritium or deuterium analog of borane which can also serve as a selective reducing agent. Each of these reducing agents can then be contacted with the organic compound having the reducible site so as to directly reduce the reducible site and introduce tritium or deuterium atoms thereinto.

In another aspect this invention provides the highly specific and selective deuterium and tritium labeling reagents just described, that is, the tritium and deuterium analogs of alkali metal trialkyl borohydride, the tritium and deuterium analogs of alkali metal aluminum hydride, and the deuterium and tritium analogs of borane.

In particularly preferred embodiments the process and reagents provided by this invention are used at very high specific activities, often approaching the theoretical maximum. Thus, this invention can provide highly specific reagents and a process for achieving high levels of deuterium and tritium in selected sites of sensitive organic compounds.

BRIEF DESCRIPTION OF THE DRAWINGS

In this description of the invention reference will be made to the drawings in which:

FIG. 1 is a tritium NMR spectrum illustrating the results of a reduction and tritium labeling possible with the process and reagents of this invention. FIG. 1 is accompanied by FIGS. 1A and 1B which are two expansions of this NMR spectrum illustrating details of it.

FIG. 2 is also a tritium NMR spectrum illustrating the results of another reduction and tritium labeling carried out using the process and reagents of this invention. This spectrum is different from the spectrum of FIG. 1 in that the concentration of tritium in the reducing agent is substantially higher. Again, FIG. 2 is accompanied by FIGS. 2A and 2B which are also expansions and details of the FIG. 2 spectrum.

FIG. 3 is a pair of high performance liquid chromatograms of the product of a reduction and labeling using the process and reagents of the present invention. This figure is made up of two traces. The first (A) is an ultraviolet trace. The second (B) is a radioactive trace.

DETAILED DESCRIPTION OF THE INVENTION

General Description and Definitions

One feature of the present invention is its ability to achieve high levels of introduction of deuterium or tritium radiolabel into target molecules. This is achieved without harsh conditions which can give rise to disruption of or nonspecific addition to the target molecules. A labeling agent having a "high tritium or deuterium level" as used herein refers to a labeling agent in which at least 20% of the reducing hydrogen atoms are tritium or deuterium. By "reducing hydrogen atom" is meant a hydrogen atom that may ultimately be transferred to the target compound at the site of reduction. "High tritium or deuterium level" is also used to refer to the reduced target compound in which at least 20% of the reducing hydrogen atoms incorporated into the molecule via reduction are tritium or deuterium atoms. In preferred embodiments, at least about 50% of the reducing hydrogen atoms present in the labeling reducing agent and subsequently incorporated into the target molecule are tritium or deuterium atoms. In specially preferred embodiments at least about 80% of the reducing hydrogen atoms present in the labeling reagent and incorporated into the target molecule are tritium or deuterium atoms.

Pure tritium has a specific activity of 28.72 Curies per milliatom (Ci/mmatom). Therefore, a highly tritiated compound, in which at least 20% of the reducing hydrogen is tritium, will have a specific activity of at least 5.74 Ci/mmole of reducible hydrogen atoms. In the preferred (50%) embodiment of this invention, the compounds will have a specific activity of at least 14.36 Ci/mmole of reducible hydrogen atoms.

An organic compound having a "reducible site" as used herein refers to a compound which has a group or functionality within its covalent structure which is capable of being reduced by the labeling reagents of this invention. The "reducible site" will receive at least one and often two or more hydrogen, deuterium or tritium atoms when acted upon by the processes and reagents of this invention. Examples of reducible sites include aldehydes which are reduced to primary alcohols, ketones which are reduced to secondary alcohols, acid chlorides which are reduced to primary alcohols, lactones which are reduced to glycols, epoxides, esters, carboxylic acids, carboxylic acid salts and tertiary amides which are all reduced to primary alcohols, nitriles and nitros which are reduced to primary amines, olefins and alkyl halides which are reduced to alkanes, aryl halides which are reduced to aryls, p-toluene sulphonates which are reduced to alkanes and $\alpha,\beta$-enones which are reduced to ketones. Table 1, which follows, summarizes these reactions and correlates them with the reactivity of a variety of hydride reagents.

TABLE 1

| | | | Reactivity of Hydride Reagents, in THF | | | | |
|---|---|---|---|---|---|---|---|
| Functional Gp. | Product | #H* | LiEt$_3$BH | Li(s-Bu)$_3$BH | LiAlH$_4$ | BH$_3$ | NaBH$_4$ |
| Aldehyde | 1° OH | 1 | + | + | + | + | + |
| Ketone | 2° OH | 1 | + | + | + | + | + |
| Acid Chloride | 1° OH | 2 | + | + | + | – | + |
| Lactone | Glycol | 2 | + | + | + | + | – |
| Epoxide | 1° OH | 1 | + | + | + | + | |
| Ester | 1° OH | 2 | + | + | + | ± | – |
| Carboxylic acid | 1° OH | 2 | – | – | + | + | – |
| Carboxylic acid salt | 1° OH | 2 | – | – | + | – | – |
| tert-Amide | 1° OH | 1 | + | + | + | + | – |
| Nitrile | 1° Amine | 2 | + | + | + | + | – |
| Nitro | NH$_2$ | (2) | + | + | + | – | – |
| Olefin | Alkane | 2 | – | – | – | × | – |
| Alkyl Halide | Alkane | 1 | + | + | + | – | + |
| Aryl Halide | CH | 1 | – | – | + | – | – |
| pToluene sulphonates | Alkane | 1 | + | + | – | – | – |
| $\alpha,\beta$ Enone | Ketone | 1 | + | + | – | – | – |

+ = reactive
± = slightly reactive
– = very slow or unreactive
× = organoborane formed a-THF,diglyme or ethanol solution In chemical formulae, tritium will be identified as T, deuterium as D and H* refers to a mixture of deuterium or tritium with hydrogen containing greater than >20% (molar) tritium or deuterium.

The term "alkali metal", as used herein refers to lithium, sodium, or potassium. Thus, an alkali metal tritide refers to LiT, NaT or KT. An "alkali metal alkyl", as used herein refers to an organometallic compound of lithium, sodium, or potassium with a simple alkyl, such as a methyl, ethyl, n or i propyl or n, s, or t butyl.

"Lower alkyl" as used herein refers to a straight chain, branched chain, cyclic or bicyclic saturated hydrocarbon containing from one to about six carbon atoms.

A "lower alkylene" as used herein refers to a generally straight chain bridging saturated hydrocarbon containing from about two to about four carbon atoms.

"Labeling reagent" as used herein refers to a compound capable of transferring a tritium or deuterium atom to a target compound in a reduction reaction.

The Labeling Reagents

It is in the area of high deuterium and tritium content H* that the present invention offers labeling reagents and methods vastly superior to materials and methods available heretofore. For that reason it is especially preferred that H* is at least 80% or as close to 100% deuterium or tritium as possible.

The labeling reagents provided by this invention are highly active reducing agents which can achieve high levels of site-specific reduction in target molecules with minimal disruption of the target molecule's structure. The reagents fall into three general classes. The first are the deuterium and tritium analogs of alkali metal trialkyl borohydrides. These materials have the formula $MR^1R^2R^3BH^*$. In this formula M is an alkali metal (as defined), preferably lithium. $R^1$, $R^2$ and $R^3$ are independently selected from lower alkyls. Preferably $R^1$, $R^2$ and $R^3$ are identical. In especially preferred embodiments $R^1$, $R^2$ and $R^3$ are each ethyl, each sec-butyl or each 1,2-dimethyl propyl. These first two materials are analogous to the "superhydride" and "selectride" reducing agents known in the art.

The second general class of reagents are deuterium and tritium analogs of alkali metal aluminum hydrides and have the formula $MAlH^*_4$ with M and $H^*$ being as defined above.

The third general class of reducing agents are deuterium and tritium analogs of borane. They have the formula $BH^*_3$ where $H^*$ is as previously defined.

Preparation and Use of the Reagents

The reagents listed above can, in theory, be prepared, isolated and stored prior to use and this practice is not excluded from the invention as claimed herein. However, best results are achieved when the reagents are prepared relatively immediately prior to use. This description of preparation and use will focus on this in situ preparation method but those of skill in the art will be able to readily adapt this to isolate the reagents if desired.

A general preparation scheme for the reagents is shown in Reaction Sequence 1.

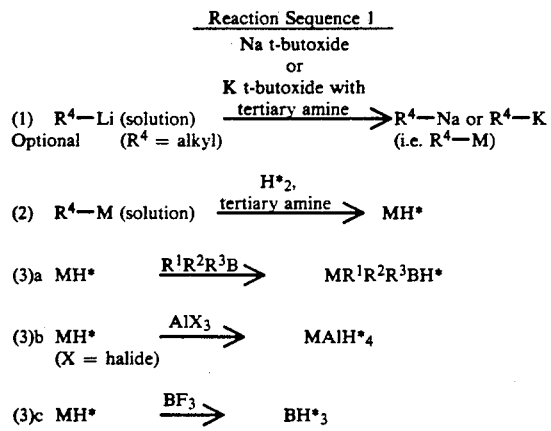

Step 1 of this preparation process is optional. It is used to form sodium and potassium materials. If lithium materials are employed, step 1 is not used. Step 1 begins with an alkyl lithium material, $R^4$-Li. In this formula $R^4$ is an alkyl, especially a lower alkyl, and more especially n-butyl. This reaction is carried out in solution. Typical solvents are saturated hydrocarbons, for example pentane, n-hexane, cyclcohexane, heptane, and saturated hydrocarbon fractions. The reaction is carried out in the presence of a tertiary amine, especially a tertiary alkyl amine, such as a tertiary lower alkyl amine. A preferred group of tertiary amines are the alkylene diamine ditertiary amines such as tetraalkylalkylenediamines. These can include materials such as tetramethylethylenediamine (TMEDA), tetraethylethylenediamine (TEEDA), tetramethylpropylene 1,3-diamine and the like. This reaction can be carried out at −10 to 50° C. and typically is carried out at 10 to 25° C. Typical reaction times range from 5 to 120 minutes with reaction time being inversely related to reaction temperature. 30 to 45 minutes at 15°–20° C. are conditions which have worked very effectively. Essentially equimolar amounts of amine, lithium, alkyl and sodium or potassium alkoxide give good results. The reaction mixture may be stirred.

In step 2 the $R^4$-M solution is contacted with $H^*_2$ in the presence of tertiary amine. The solvent and tertiary amine may already be present from step 1. This reaction is carried out with about 1 mole of tertiary amine present for each mole of $R^4$-M. Generally an excess of $H^*_2$ is employed. This can be achieved by conducting the reaction under a substantial pressure, e.g. 0.25 to several (10) atmospheres, of $H^*_2$. Most preferred pressures are in the range of 0.5 to 2 atmospheres of $H^*_2$, primarily because of a convenient rate of reaction, and simplicity of laboratory equipment and handling under these conditions.

This reaction goes quite rapidly and has a tendency to be substantially exothermic. Accordingly, vigorous stirring is desirable as well as cooling to hold the temperature in the desired range. The sodium and potassium reactions are somewhat more violent and are usually held in the −50° C. to −10° C. temperature range during initial $H^*_2$ addition. They can be allowed to warm to room temperature during later stages. The lithium reaction can be held at room temperature (15°–25° C.) to about 50° C. without hazard. This reaction is complete within about 60 minutes in most cases. In this reaction it is helpful if all solvents and reagents are quite dry. These $MH^*$ materials are pyrophoric in air. Accordingly they should be kept covered with an inert atmosphere if isolated.

In the third step of Reaction Sequence 1 the metal hydride produced in step 2 is converted to an active reducing agent. In reaction 3A the metal hydride is reacted with a trialkyl borane. This can be carried out directly in the reaction mixture of step 2 following uptake of $H^*_2$. Essentially an equimolar amount of the trialkyl borane is added based on the moles of $MH^*$ present. This reaction can be carried out at room temperature (15°–25° C.) and appears to be complete within a few seconds. Higher or lower temperatures could be used if desired. This reaction mixture as so formed can be used directly in the reduction and labeling of a reducible target compound.

In reaction 3B, it is generally desirable to first isolate the $MH^*$ intermediate, such as by removing solvent in vacuo and capping with nitrogen gas. To this solid material can then be added the stoichiometrically required amount of aluminum trihalide, for example aluminum tribromide in a suitable solvent such as an aprotic polar solvent for example THF, DMF or DMSO. In a typical process, $AlBr_3$ is obtained in solution in dibromomethane. The solvent is removed and the solid $AlBr_3$ is then dissolved in THF with cooling to −50° C. to 0° C. When the solution of aluminum salt is mixed with the $MH^*$ to give the metal aluminum hydride the reaction is very rapid and is carried out at low to moderate temperatures, typically in the range of −20° to 35° C. and especially at about room temperature. This material as formed can be used directly in the reductive labeling.

In the case of reaction 3C, again it is desirable to first isolate the $MH^*$ material. The reaction of the $MH^*$ with $BF_3$, which $BF_3$ is generally present as an etherate (Et- $_2O \cdot BF_3$), is typically begun at low temperature, such as $-50°$ C. to $0°$ C. This is to allow a gradual controlled evolution of the ether, which is released as the $BF_3$ decomposes and reacts. The mixture is allowed to warm to room temperature or even beyond, such as to $50°$ C. to complete the reaction and yield a solution of the desired borane analog. This material can be used directly in the reductive labeling.

Use of the Reagents

As detailed in the Examples which follow, the reagents prepared by reactions 3A, 3B and 3C are all highly reactive materials. They can be used with a wide variety of target compounds having a reducible site so as to introduce deuterium or tritium labels thereinto. In a typical reaction the products of reactions 3A, 3B or 3C are used directly in approximately the stoichiometric amount required to add the labeling deuterium or tritium atoms. This reaction can be carried out generally at room temperature, for example from about $10°$ C. to about $35°$ C. and is complete in from about 10 to about 30 minutes.

Following reaction, the labeling reaction mixture is quenched such as by addition of methanol or the like, and the product is then worked up to recover the labeled reducible target.

This invention will be further described by the following examples. These are provided to illustrate various preferred embodiments of the invention but are not to be construed as limitations on the scope of the invention. The scope of the invention is defined by the claims which follow.

EXAMPLES

Tritium gas was purchased from Oak Ridge National Laboratory, and contained 97.9% $T_2$, with the largest contaminant being DT (1.76%). Ethyl-p-nitrobenzoate was purchased from ICN, and all other starting materials and reagents were purchased from Aldrich Chemical Co. All chemicals were used without further purification. n-Butyllithium (1.6M in hexane) was purchased from Aldrich, titrated with 2,5-dimethoxybenzylalcohol and determined to be 1.2M. Tetrahydrofuran was freshly distilled from $LiAlH_4$ and stored over molecular sieves. Tritiated samples were counted with a Packard 2002 liquid scintillation counter, using Opti-Fluor scintillant from Packard. Thin layer chromatography was carried out on Whatman K6F analytical silica gel plates (250 $\mu$m), using dichloromethane/hexane (2:1) as developing solvent. Analytical high pressure liquid chromatography was performed by using a Waters C-18 radial pak column, and Waters model 510 pumps. The HPLC mobile phase for analysis of most of the products was 60% methanol/water, pumped at 2 ml/min. Mass peaks were observed by UV detection at 275 nm on a Hewlett Packard 1040A diode array spectrophotometer. Radioactivity measurements were made with a Ramona-5-LS HPLC flow detector, using a lithium glass scintillant cell with an efficiency of ca. 0.05%. $^1H$ and $^3H$ NMR spectra were recorded in $CD_3OD$, on an IBM AF-300 NMR spectrometer ($^3H$ at 320 MHz, $^1H$ at 300 MHz), using a $^3H/^1H$ 5 mm dual probe. Samples were made to a volume of 200 $\mu$L in teflon tubes (Wilmad, #6005), which were then placed inside 5 mm glass NMR tubes having a screw-cap (Wilmad, 507-TR-8"). A quality $^3H$ band stop-$^1H$ band pass filter (Cir-Q-Tel Inc., FBT/20-300/3-6/50-3A/3A) was placed in the proton decoupling line of the instrument, and the observe channel had an in-line $^1H$ band stop-$^3H$ band pass filter. Tritium and proton spectra were acquired over approximately 12 ppm, using a 5 s total recycle time and excitation pulses of 3.6 $\mu$s (3H, 65°) and 2 $\mu$s ($^1H$, 25°). All spectra were acquired at $297°$ K. with the sample spinning. Referencing of tritium chemical shifts was achieved by generation of a ghost $^3H$ TMS signal from internal TMS in the $^1H$ NMR spectrum.

Tritiations were performed on several different chemical scales, but were generally 1 mmol scale using 10% $T_2$ in $H_2$, and 0.1–0.2 mmol scale using 100% $T_2$. Reactions were carried out at room temperature, unless otherwise noted, in 5–15 mL side-arm flasks equipped with a septum. The reaction pressure was monitored with a Wallace & Tiernan gauge, and the reaction vessel was connected to a high vacuum line during the entire reaction. The results of these examples are summarized in Table 2 which follows Example 9.

EXAMPLE 1

Reaction of 2-Naphthaldehyde with Supertritide 10%

A 10% mixture of tritium/hydrogen was admitted to a final pressure of 650 mm Hg (91.5 kPa) to a flask containing n-butyllithium solution (n-BuLi, 630 $\mu$L, 1.2M in hexane, 0.75 mmol). Injection of tetramethylethylenediamine (TMEDA, 150 $\mu$L, 1.0 mmol) to the vigorously stirred solution gave a creamy white precipitate (LiT and LiH) after 15 minutes. It was observed that hydrogen gas uptake was more rapid when the reaction pressure was maintained above 360 mm Hg (51 kPa), so additional tritium/hydrogen gas was admitted to the flask after 15 minutes. After 30 minutes, uptake of tritium/hydrogen had ceased and triethylborane (1M, 1 mL, 1 mmol) in tetrahydrofuran (THF) solution was injected to generate the $LiEt_3BT$ (supertritide) reagent. At this point there was a pressure increase, and the creamy suspension clarified within a few seconds. A THF solution of 2-naphthaldehyde (160 mg, 1 mL, 1 mmol) was slowly added with stirring and allowed to react with the supertritide for 30 minutes at room temperature. At the end of the reaction, methanol ($2 \times 1$ mL) was added to quench the supertritide reagent and solvent and gas were removed in vacuo. Methanolic HCl (1 mL of a solution of 1.5 mL 1N HCl and 1 mL MeOH) was added to destroy any borane complexes and the pressure rose considerably, indicating the evolution of ethane. The solvent and gases were evacuated, and the reaction products were then removed from the vacuum line, dissolved in ethyl acetate (1 mL), and the borate salts were separated by washing with KOH ($2 \times 1$ ml, 0.1N). EtOAc was removed by overnight lyophilization, and the residual solids were dissolved $CD_3OD$ for liquid scintillation counting, TLC, HPLC, and NMR analyses.

All analyses (TCL, HPLC AND NMR) of this product suggested that generation of the supertritide reagent had been successful and conversion of the aldehyde to product alcohol was quantitative, though with a moderate chemical yield (24%). It was determined that there were several yield limiting factors in this initial reaction including (a) the true molarity of the n-BuLi, (b) the dryness and purity of the TMEDA, and (c) the dryness of the THF solvent. These were addressed in Example 2.

EXAMPLE 2

Reaction of Methyl 2-Naphthoate with Supertritide 20%

The supertritide reagent was generated by stirring n-BuLi (415 μL, 1.2M, 0.5 mmol) and TMEDA (85 μL) in the presence of one atmosphere of tritium gas (20% T), and subsequent addition of $Et_3B$ (0.5 mL, 1M, 0.5 mmol) in THF after approximately 30 minutes, when gas uptake had ceased. Methyl 2-naphthoate (94.5 mg, 0.5 mL, 0.51 mmol) was added as a THF solution. The reaction was stopped after two hours by the addition of methanol (1 mL), with subsequent methanolic HCl treatment and workup of the reaction products carried out in a similar fashion as that described above.

The product was analyzed by tritium NMR. The spectrum so obtained is given in FIG. 1. Inset (A) shows an expansion (4.85–4.60 ppm) of the proton decoupled tritium spectrum, with the smaller singlet due to molecules containing two tritium atoms. Inset (B) shows the proton coupled tritium spectrum, with a doublet for the R-CHTOH species ($J_{TH}$=13.83 Hz) and singlet arising from $R-CT_2OH$ molecules. The ratios of singly and doubly tritiated products calculated from this spectrum was as expected if there were no isotope effect. ($H_2/HT/T_2$=64/32/4). That is, the percentage of $R-CT_2OH$ and R-CHTOH species should have been 4% and 32% respectively with $^3H$ NMR signals having intensities of 8:32 as observed (21:100) within the accuracy of the original T/H gas mixture.

EXAMPLE 3

Reaction of Methyl 2-Naphthoate with Sucertritide 100%

Tritium gas (100%) was admitted to a final pressure of 650 mm Hg (91.5 kPa) to a flask containing 3 μL (0.1 mmol) of n-BuLi solution (1.2M in hexane). Injection of TMEDA (20 μL, 0.1 mmol) to the stirred solution gave a creamy white precipitate (LiT). Since the scale of this reaction was much smaller than the above examples, it was not necessary to add additional tritium gas to keep the reaction pressure above 360 mm Hg (51 kPa). After 30 minutes uptake of tritium had ceased and triethylborane (0.1 mL, 1M in THF, 0.1 mmol) was injected, generating the $LiEt_3BT$ reagent, giving a slight pressure increase, and causing clarification of the creamy solution. A THF solution of methyl 2-naphthoate (100 μL, 9.7 mg, 0.05 mmol) was slowly added, and allowed to react with the supertritide at room temperature, with stirring, for 30 minutes. At the end of the reaction, methanol (3×0.5 mL) was added to quench the supertritide reagent, and both solvent and gas were removed in vacuo. Methanolic HCl was added, and removed in vacuo. The reaction products were then removed from the vacuum line, and worked up as for the larger scale, lower activity samples.

This product was analyzed by tritium NMR. The spectrum so obtained is given in FIG. 2. Inset (A) shows an expansion (4.85–4.60 ppm) of the proton decoupled tritium spectrum, with the smaller singlet in this case due to molecules containing only one tritium atom. Inset (B) shows an expansion from 5.1–4.4 ppm, with larger vertical scale. Note the $^{13}C$ satellite peaks (asterisks) with $J_{CT}$=149.89 Hz, which help to give scale to the abundance of the singly labeled species. This product had a specific activity 95% of theoretical (as shown by HPLC and counting). NMR studies (FIG. 2.) supported this analysis, showing a trace of $R-CH_2OH$ and R-CHTOH species in the proton NMR spectrum (the tritiated isotopomer being slightly isotope shifted upfield), and the R-CHTOH peak having 3.4% the intensity of the $RCT_2OH$ peak in the spectrum of FIG. 2.

EXAMPLE 4

Reaction of Ethyl p-Nitrobenzoate with Supertritide 10%

The supertritide reagent was generated at 0.2 mmol scale, using 166 μL n-BuLi, 34 μl TMEDA and 200 μL 1M $ET_3B$. This reagent was then syringed into a THF solution of ethyl p-nitrobenzoate (inverse addition, 20.6 mg, 0.1 mmol, 300 mL) in an adjacent flask in order to inhibit amine formation. This particular reaction was maintained at −15° C. to control the reaction rate over the one hour reaction time. Workup of the reaction products was carried out in the same fashion as described above.

The results of Examples 1–4 demonstrate the potential of the supertritide reagent for aldehyde and ester reductions. They also show that specific activity is retained with chemoselective reduction. The ester group of ethyl p-nitrobenzoate was successfully reduced while the nitro functionality was preserved.

EXAMPLE 5

Reaction of Methyl 2-Naphthoate with Lithium Aluminum Tritide (LAT) 10%

The LiT/LiH reagent was generated at 1 mmol scale (830 μL n-BuLi, 170 μL TMEDA). After one hour of stirring both the excess gas and solvent were removed in vacuo,. and nitrogen gas was admitted to a pressure of kPa. In a separate reaction flask, solvent was removed from a solution of aluminum tribromide in dibromomethane (1M $AlBr_3$, 250 μL, 0.25 mmol), and the solid was dissolved in 1 mL THF at −20° C. to form a brownish solution. To the remaining solid LiT/LiH, 900 μL of the $AlBr_3$ solution was added slowly, yielding a tan-colored solution of LAT. A THF solution of methyl injected, and allowed to react with the LAT at room temperature, with stirring for one hour. At the end of the reaction, methanol (1 mL) was added to quench the LAT reagent, and gas evolution indicated the presence of residual hydride. The solution turned straw yellow, and the solvent volume was then reduced under vacuum. Methanolic HCl (1 mL 10% conc. HCl in MeOH) was injected, and again the solvent was removed in vacuo. The product was removed from the vacuum line and subjected to EtOAc extraction and KOH workup as described for earlier samples.

Radio HPLC and UV HPLC data were obtained on this product and are given in FIG. 3. Trace (A) is the UV trace obtained by monitoring at 275nm. Trace (B) is the radioactive trace from the in-line solid scintillant detector. The traces are slightly offset in time since the sample passes through the UV cell before the radioactivity detector. These results show that the reaction is quantitative and clean.

EXAMPLE 6

Reaction of Methyl 2-Naphthoate with Lithium Aluminum Tritide (LAT) 100%

The LiT reagent was generated as for Example 3, the excess gas and solvent were removed in vacuo. and nitrogen gas was added to 100 kPa pressure. In a separate reaction flask, solvent was removed from a solution of aluminum tribromide in dibromomethane (1M AlBr₃, 250 μL, 0.25 mmol), and the solid was dissolved in 1 mL THF at −20° C. To the solid LiT, 60 μL of the AlBr₃ solution was added with an additional 200 μL THF, and the solution clarified. A THF solution of methyl 2-naphthoate (9.1 mg, 0.05 mmol, 100 μL) was slowly added, and allowed to react with the LAT at room temperature, with stirring for one hour. At the end of the reaction, methanol (1 mL) was added to quench the LAT reagent, and the sample underwent methanolic HCl (1 mL) and EtOAc workup as above.

Examples 5 and 6 show that LiAlT₄ as reducing agent gave excellent conversion and yielded products of theoretical specific activity. Care should be exercised in the choice of stoichiometry for the generation of LiAlT₄ so as to ensure that neither LiT nor AlT₃ are the active agents.

EXAMPLE 7

Reaction of Ethyl p-Nitrocinnamate with Selectride 10%

This reaction was similar to the procedure of Fortunato, J. M., et al., supra. The LiT/LiH reagent was generated by stirring n-BuLi (830 μL) and TMEDA (170 μL) in the presence of one atmosphere of 10% T/H for one hour, and the flask was evaporated to dryness. Nitrogen gas was admitted to 100 kPa, and the LiH /LiT was reacted with tri-sec-butylborane (1M, 1 mL, 1.0 mmol) in THF, to give a turbid solution of Li(sec-Bu)₃BT. The reaction flask was cooled to −78° C., and 2.5 mL of a solution of ethyl p-nitrocinnamate (221 mg, 1 mmol) and t-butyl alcohol (266 mg) was slowly added to give a green solution. After 20 minutes the reaction temperature had risen to −70° C., and the reaction was quenched with methanol to give an orange product. The solvent and excess gases were removed by evacuation. Oxidative workup (to destroy the borane complex) was achieved by the addition of NaOH (1 mL, 2N), H₂O₂ (1 mL, 30%) and hexane (5 mL) with stirring overnight at room temperature. This yielded a precipitate, which was extracted by the addition of EtOAc. The organic layer was lyophilized, dissolved in MeOH, relyophilized and dissolved in CH₂Cl₂. The product was then chromatographed on a 25 mL silica column, and developed with CH₂Cl₂. Five fractions (each 10 mL) were collected and counted, and fractions 1 and 2 were found to contain the product with the most radioactivity. These were combined, lyophilized, and dissolved in CD₃OD for HPLC and NMR analyses. HPLC was conducted using a mobile phase of 80% CH₃OH in H₂O at 2 mL/min.

This shows the utility of L-Selectride in tritium labeling experiments, making use of the outstanding selectivity of this reagent. In a 1,4 addition, the double bond of ethyl p-nitrocinnamate was reduced without affecting the nitro functional group. Some of the ester functionality appeared to have been hydrolyzed (by NMR analysis). Much less than 5% of the incorporated tritium was in the alpha-CH₂ position, giving effectively quantitative tritiation in the CH₂ position beta to the ester group. The specific activity of this sample was not calculated from the HPLC analyses, since an authentic standard was not freely available.

EXAMPLE 8

Reaction of Naphthoic Acid and Methyl Myristate with Borane 10%

The LiT/LiH reagent was generated as for Example 7 and solvent and gas were removed by evaporation. Nitrogen was admitted to 100 kPa and Et₂O·BF₃ (164 μL, 1.3 mmol) was added at −20° C. The white solid dissolved rapidly as the solution was warmed to room temperature. After 30 minutes, borane (BH₂T) was removed by vacuum distillation to an adjoining flask, which contained a THF solution (300 μL) of methyl myristate (12.5 mg, 0.05 mmol) and naphthoic acid (21.7 mg, 0.125 mmol). The reaction was allowed to proceed at room temperature, with stirring for 45 minutes. At the end of the reaction, H₂O (0.2 mL) was added to quench the borane reagent, the pressure rose significantly, and both solvent and gas were removed in vacuo. Methanol (2×0.6 mL) was injected and evaporated, followed by dissolution in ethyl acetate and extraction with NaOH (1N) as described in earlier examples. HPLC analysis of the products was achieved by monitoring at 215 nm and using a methanol/water mobile phase as follows: 60% CH₃OH for 10 minutes, gradient to 100% CH₃OH for a further five minutes.

EXAMPLE 9

Reaction of Naphthoic Acid with Borane 100%

The LiT reagent was generated as above at 0.2 mmol scale and solvent and gas were subsequently removed by evaporation. Nitrogen was admitted to 90 kPa and THF (200 μL) was injected. Et₂O·BF₃ (33 μL, 0.26 mmol) was added at room temperature, and there was an immediate pressure rise as the solution turned to a turbid white mixture. A THF solution of 2-naphthoic acid (17 mg, 0.1 mmo, 200 μl) was slowly injected with cooling. The reaction was allowed to proceed at room temperature, with stirring for 20 minutes. At the end of the reaction, methanol (1 ml) was added to quench the borane reagent, the pressure rose significantly, and both solvent and gas were removed in vacuo. Methanolic HCl (1 mL, 10%) was injected and evaporated, followed by dissolution in ethyl acetate and extraction with KOH (1N) as described in earlier examples.

Example 8 shows that borane is a selective reagent, able to reduce acids in the presence of esters. Both the HPLC and NMR analyses were in agreement that some 10% of the product radioactivity was due to reduced ester. Tritium NMR study suggested that the R-CT₂OH to R-CHTOH ratio in the product was very close to the theoretical, while the specific activity of the product appeared to be considerably higher than theoretical (9.6 vs 5.76 Ci/mmol). Example 9 shows that borane reagents perform similarly when at almost theoretical maximum specific activity.

TABLE 2

| | | Reactions of Tritide Reagents | | | |
|---|---|---|---|---|---|
| Reagent R_x (% T/H) | Precursor and Product | S.A. Ci/mmole (Theor. Value) | Yield % | Comments on HPLC | NMR Data |
| 1. LiEt₃BT (10%) | 2-Naphthaldehyde 2-(Hydroxymethyl)naphthalene | 2.42 (2.88) | 24 | Aldehyde 3% of UV. No other peaks in ³H. | δ=4.7020, J_{HT}=13.81Hz |

TABLE 2-continued

Reactions of Tritide Reagents

| $R_x$ | Reagent (% T/H) | Precursor and Product | S.A. Ci/mmole (Theor. Value) | Yield % | Comments on HPLC | NMR Data |
|---|---|---|---|---|---|---|
| 2. | LiEt$_3$BT (20%) | Methyl 2-Naphthoate 2-(Hydroxymethyl)naphthalene | 13.4 (11.52) | 68 | Acid 11% of UV. No other peaks in $^3$H. | $\delta_1$=4.7145, $\delta_2$=4.6833, $J_{HT}$=13.83Hz 1° isotope effect=9.99Hz % CHT=100, % CT$_2$=21.00 |
| 3. | LiEt$_3$BT (100%) | Methyl 2-Naphthoate 2-(Hydroxymethyl)naphthalene | 54.2 (57.6) | 27 | Ester 3.7% of UV. No other peaks in $^3$H. | $\delta_1$=4.7445, $\delta_2$=4.7133 1° isotope effect=9.98Hz % CHT=3.37, % CT$_2$=100 |
| 4. | LiEt$_3$BT (10%) | Ethyl p-Nitrobenzoate p-Nitrophenyl benzyl alcohol | 7.1 (5.76) | 26 | Small peak at 7 min RT, $^3$H and UV. UV similar to benzyl alcohol. | $\delta_1$=4.7088, $\delta_2$=4.6762, $J_{HT}$=15.38Hz 1° isotope effect=10.44Hz % CHT=100, % CT$_2$=9.51 |
| 5. | LiAlT$_4$ (10%) | Methyl 2-Naphthoate 2-(Hydroxymethyl)naphthalene | 8.5 (5.76) | 66 | Some small peaks in UV. No other peaks in $^3$H. | $\delta_1$=4.7346, $\delta_2$=4.7033, $J_{HT}$=13.82Hz 1° isotope effect=10.02Hz % CHT=100, % CT$_2$=9.49 |
| 6. | LiAlT$_4$ (100%) | Methyl 2-Naphthoate 2-(Hydroxymethyl)naphthalene | 60.5 (57.6) | 38 | Ester 9.4% of UV. No other peaks in $^3$H. | $\delta_1$=4.7425, $\delta_2$=4.7113 1° isotope effect=10.01Hz % CHT=3.48, % CT$_2$=100 |
| 7. | Li(s-Bu)$_3$BT (10%) | Ethyl p-Nitrocinnamate Ethyl p-Nitrophenyl propanoate | — (2.88) | <10 | 3 other small peaks in the UV. | $\delta_1$=3.0444, $J_{HT}$=12.6Hz |
| 8. | BT$_3$ (10%) | 2-Naphthoic Acid/ Methyl Myristate 2-(Hydroxymethyl)naphthalene | 8.9 (5.76) | 100 | Methyl Myristate had 9% of the UV, and 8.8% of the $^3$H intensity. | $\delta_1$=4.7453, $\delta_2$=4.7140, $J_{HT}$=13.82Hz 1° isotope effect=10.01Hz % CHT=100, % CT$_2$=11.96 |
| 9. | BT$_3$ (100%) | 2-Naphthoic Acid 2-(Hydroxymethyl)naphthalene | 55.0 (57.6) | 2.5 | Product had 13.3% of the UV, and 41% of the $^3$H intensity. | $\delta_1$=4.7500, $\delta_2$=4.7186, $J_{HT}$=13.82Hz 1° isotope effect=10.05Hz % CHT=2.46, % CT$_2$=100 |

What is claimed is:

1. A process for introducing high activity levels of tritium radiolabel into an organic compound having a chemically reducible site comprising
    a) reacting an organic solvented solution of alkali metal alkyl with gas comprising at least about 20% molar tritium gas in the presence of an alkyl tertiary amine thereby giving rise to high activity alkali metal tritide,
    b) reacting the high activity alkali metal tritide of step a and a solution of aluminum halide thereby forming a solution of high activity alkali metal aluminum tritide and
    c) thereafter admixing the solution of high activity alkali metal aluminum tritide with the organic compound having a chemically reducible site thereby directly reducing the chemically reducible site by introducing tritium atoms of the tritide thereinto in an amount equal to at least about 20% of the total reducing atoms introduced.

2. The process of claim 1 wherein in step a the alkali metal is lithium.

3. The process of claim 2 wherein in step b the aluminum halide is aluminum bromide.

4. The process of claim 3 wherein in step a the alkyl tertiary amine is a tetra(lower alkyl) lower alkylenediamine.

5. The process of claim 4 wherein in step a the gas comprising at least about 20% mole tritium gas contains from 80 to 100% tritium gas.

6. The process of claim 4 wherein the tetra lower alkyl lower alkylene diamine is selected from tetramethylethylenediamine and tetraethylethylenediamine.

7. The process of claim 1 wherein in step a the gas comprising at least about 20% mole tritium comprises from 80 to 100% mole tritium.

8. The process of claim 7 wherein in step a the gas comprising from 80 to 100% mole tritium consists essentially of tritium.

9. A process for introducing high activity levels of tritium radiolabel into an organic compound having a chemically reducible site comprising
    a) reacting a saturated hydrocarbon solvented solution of n-butyl lithium with a gas comprising at least about 80% molar tritium and the remainder essentially hydrogen in the presence of a tetra lower alkyl lower alkylene diamine thereby giving rise to high activity lithium tritide,
    b) reacting the high activity lithium tritide of step a with a solution of aluminum halide thereby forming a solution of high activity lithium aluminum tritide and,
    c) thereafter admixing the solution of high activity lithium aluminum tritide with the organic compound having a chemically reducible site thereby directly reducing the chemically reducible site by introducing tritium atoms of the tritide thereinto in an amount equal to at least about 80% of the total reducing atoms introduced.

* * * * *